(12) United States Patent
Kemper et al.

(10) Patent No.: US 12,059,291 B2
(45) Date of Patent: Aug. 13, 2024

(54) TRAUMA ULTRASOUND REDUCTION DEVICE

(71) Applicant: Stryker European Operations Limited, Carrigtwohill (IE)

(72) Inventors: Jakob Kemper, Heemstede (NL); Andreas Heede, Neumünster (DE); Oliver Kutter, Bad Krozingen (DE); Clinton Siedenburg, Everett, WA (US); Peter Sterrantino, Jacksonville, FL (US)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 17/629,237

(22) PCT Filed: Jul. 22, 2020

(86) PCT No.: PCT/IB2020/000603
§ 371 (c)(1),
(2) Date: Jan. 21, 2022

(87) PCT Pub. No.: WO2021/014211
PCT Pub. Date: Jan. 28, 2021

(65) Prior Publication Data
US 2022/0265243 A1    Aug. 25, 2022

Related U.S. Application Data

(60) Provisional application No. 62/877,609, filed on Jul. 23, 2019.

(51) Int. Cl.
*A61B 8/08*     (2006.01)
*A61B 5/00*     (2006.01)
(Continued)

(52) U.S. Cl.
CPC .......... *A61B 8/0875* (2013.01); *A61B 5/1077* (2013.01); *A61B 5/4504* (2013.01);
(Continued)

(58) Field of Classification Search
CPC ... A61B 8/0875; A61B 5/1077; A61B 5/4504; A61B 8/4209; A61B 8/4281;
(Continued)

(56) References Cited

U.S. PATENT DOCUMENTS 6,964,639 B2    11/2005    Sela et al.
8,202,219 B2     6/2012    Luo et al.
(Continued)

FOREIGN PATENT DOCUMENTS

CN    102793562 A    11/2012
CN    106913357 A     7/2017
(Continued)

OTHER PUBLICATIONS

International Search Report and Written Opinion for Application No. PCT/IB2020/000603 dated Oct. 5, 2020, 12 pages.
(Continued)

*Primary Examiner* — Alexei Bykhovski
(74) *Attorney, Agent, or Firm* — Lerner David LLP

(57) ABSTRACT

A body profiling system includes multiple pivotally connected links and multiple probes. Each of the probes is disposed on one of the links and includes any one or any combination of a transmitter configured to send a signal, a receiver configured to receive the signal, and a transceiver configured to send and receive the signal.

20 Claims, 7 Drawing Sheets

(51) Int. Cl.
  *A61B 5/107* (2006.01)
  *A61B 8/00* (2006.01)
(52) U.S. Cl.
  CPC .......... *A61B 8/4209* (2013.01); *A61B 8/4281* (2013.01); *A61B 8/4477* (2013.01); *A61B 8/565* (2013.01)
(58) Field of Classification Search
  CPC ......... A61B 8/4477; A61B 8/565; A61B 8/00; A61B 5/4547
  See application file for complete search history.

(56) References Cited

U.S. PATENT DOCUMENTS

| | | |
|---|---|---|
| 2012/0300578 A1 | 11/2012 | Sakaguchi |
| 2015/0051490 A1 | 2/2015 | McKinnon et al. |
| 2015/0133788 A1* | 5/2015 | Mauldin, Jr. ........ A61B 8/4281 600/444 |
| 2015/0374334 A1 | 12/2015 | Klock et al. |
| 2016/0166234 A1* | 6/2016 | Zhang ................. A61B 8/4209 600/443 |
| 2016/0242736 A1 | 8/2016 | Freiburg et al. |
| 2017/0079386 A1* | 3/2017 | de Iuliis ............. G04B 37/1486 |
| 2017/0100092 A1* | 4/2017 | Kruse ................... A61B 8/085 |
| 2017/0311808 A1 | 11/2017 | Thornton et al. |
| 2018/0249986 A1* | 9/2018 | Lee .......................... A61B 8/54 |
| 2019/0001159 A1* | 1/2019 | Chen ..................... A61B 8/085 |
| 2020/0405218 A1* | 12/2020 | Avila ................... A61B 5/0004 |

FOREIGN PATENT DOCUMENTS

| | | |
|---|---|---|
| CN | 107613882 A | 1/2018 |
| CN | 107635470 A | 1/2018 |
| EP | 3456268 A1 | 3/2019 |
| JP | S61-062447 A | 3/1986 |
| JP | H08-182674 A | 7/1996 |
| JP | 2005-137581 A | 6/2005 |
| JP | 2014-233597 A | 12/2014 |
| WO | 1997013145 A1 | 4/1997 |

OTHER PUBLICATIONS

Search Report dated Feb. 22, 2024 from Office Action for Chinese Application No. 202080062068.6 issued Feb. 23, 2024. 3 pgs.

* cited by examiner

TRAUMA ULTRASOUND REDUCTION DEVICE

CROSS REFERENCE TO RELATED APPLICATIONS

The present application is a national phase entry under 35 U.S.C. § 371 of International Application No. PCT/IB2020/000603, filed Jul. 22, 2020, which claims priority from U.S. Provisional Patent Application No. 62/877,609, filed on Jul. 23, 2019, the disclosures of which are incorporated herein by reference.

FIELD OF THE INVENTION

The present application relates generally to the assessment of bone fractures, and in particular, to a body profiling system for assessing such fractures through the use of ultrasound.

BACKGROUND OF THE INVENTION

The nature and dislocation of a bone fracture should be assessed prior to treating fracture. To that end, multiple technologies exist for imaging bone fractures in injured patients, including x-ray imaging, computed tomography (CT) scans, fluoroscopy, and magnetic resonance imaging (MRI) scans. Today, such technologies provide for often high resolution images of bone fractures. However, x-ray imaging, CT scans, and fluoroscopy expose the patient and the treating physicians and other medical practitioners to potentially harmful radiation. The number of perspectives and duration of imaging data obtained with these technologies is generally limited to avoid excessive radiation exposure. Live tracking of a fracture reduction is thus prohibitive.

Direct visualization avoids these issues. However, such visualization requires the exposure of the fracture and thus cannot be used for a closed reduction. Moreover, even when a bone fracture has been exposed, such exposure is generally only partial due to extensive tissue coverage that prevents the visualization of a fracture reduction at the far side of the surgical access.

Thus, new imaging technologies are needed to prevent radiation exposure while still providing useful images of bone fractures that allow for appropriate assessment to treat such fractures.

BRIEF SUMMARY OF THE INVENTION

In accordance with an aspect of the present disclosure, an object profiling device, which may be either one or both of an imaging device and a measuring device may include a ring or linkage provided by a series of discrete, rigid links that may be pivotally or hingedly connected in series. Each link may include a probe, which may be, for example, an ultrasound transmitter, receiver, or transceiver. In some arrangements, the probes may be located on a patient-facing surface of each link. In some examples, the patient-facing surface may be an inwardly facing or concave surface along an arc or circle defined by the linkage, while in other examples the patient-facing surface may be flat or even convex. The linkage may have a self-closing or self-constricting tendency that may be provided by commonly oriented biasing elements in each hinge or other pivotal connection of the linkage. Such biasing elements may be springs, electric motors, electromechanical actuators, and the like. The biasing elements may be operable to conform the device to a shape of a part of the patient being measured.

The profiling device may measure data including, for example, signal data from the probes and the angular positions of the pivotal connections or hinges. Such data may be used for imaging internal features of a patient being measured such as one or more bones of the patient to assess a bone fracture or other bone defect. Such assessments may be particularly useful in preparation for a surgery. The imaging may be accomplished by processing signals, such as ultrasonic or other acoustic signals transmitted between and received by certain of the probes, which may be provided by or distributed among one or more of onboard processors included in the device and remote computer systems.

In another aspect, a body profiling system may include a plurality of pivotally connectable links and a plurality of probes. Each probe of the plurality of probes may be disposed on a link. Each of the probes may include any one or any combination of a transmitter configured to send a signal, a receiver configured to receive a signal, and a transceiver configured to send and receive the signal.

In another aspect, the system may include a plurality of hinges. Each of the hinges may be attachable to adjoining links of the plurality of links to define pivot axes such that the adjoining links pivot about the respective pivot axis defined by the hinge to which the adjoining links are attached.

In some arrangements, at least one of the hinges may include a spiral spring configured to be coiled around the corresponding pivot axis.

In some arrangements, at least one of the hinges may include an electromechanical actuator configured to pivotally bias the adjoining links.

In some arrangements, the hinges may be configured to measure an angular position between adjacent links.

In some arrangements, each of the links may include a rigid enclosure.

In some arrangements, the signals may be acoustic.

In some arrangements, the device may include an acoustical coupling fluid applied to the flexible cover.

In some arrangements, the plurality of links may be connected to form a linkage. The system may further include a flexible cover that completely covers the linkage.

In some arrangements, the system may include an acoustical coupling fluid applied to the flexible cover.

In some arrangements, some of the links may be middle links pivotally connected to two adjacent links, and two of the links may be terminal links pivotally connected to only one adjacent link.

In some arrangements, the terminal links may be connected to each other by an elastic strap.

In accordance with another aspect, a body profiling system may include the device of any of the foregoing aspects and a processor. In some such arrangements, the links may be modularly and operatively interconnectable with each other to reversibly and operatively connect a new link to one of the terminal links and thereby convert the one of the terminal links to a middle link and the new link to a new terminal link. In other such arrangements, the links may be reversibly and operatively disconnected from one of the terminal links and thereby convert the adjacent link to the one terminal link to a new terminal link. The processor may be configured for determining a number of operatively connected links and electronically communicating with the plurality of probes.

In some arrangements, one of the terminal links may house the processor.

In some arrangements, the system may include a computer system that includes the processor. The processor may be located remotely from the plurality of links.

In some arrangements, at least some of the plurality of probes may be configured to communicate wirelessly with the computer system.

In accordance with another aspect, a body profiling system may include the device of any of the foregoing embodiments and a processor. In some such arrangements, the plurality of links may be connected to form a linkage. A first link may include a first transmitter, and a second link may include a first receiver. The first receiver may oppose the first transmitter such that the first receiver may receive a first ultrasonic signal from the first transmitter. A third link may include a second transmitter and a fourth link may include a second receiver. The second receiver may oppose the second transmitter such that the second transmitter may receive a second ultrasonic signal from the second transmitter. The processor may be configured for electronically communicating with the first and the second transmitters and the first and the second receivers to determine a position of an object at least partially surrounded by the system. In some arrangements, the object may be one or more bones or bone fragments of a patient.

In accordance with another aspect of the present disclosure, bone fragments of a patient may be tracked. In such aspect, a profiling device may be positioned near a part of a body of the patient that includes the bone fragments. At least one biasing element of the profiling device may be allowed to conform the profiling device to the part. Acoustic signals transmitted across the bone fragments may be interpreted to ascertain either one or both of a relative location and a relative orientation of the bone fragments.

In another aspect, a central radius of a generally arcuate shape of the profiling device may be reduced when the profiling device is conformed to the part.

In another aspect, the method may include dilating the profiling device in opposition to the at least one biasing element prior to the positioning step.

In another aspect, the profiling device may include a plurality of links. Each of the links may be joined to at least one other link by a hinged connection to form linkages. Each hinged connection may include one of the at least one biasing elements, and each of the biasing elements may be configured to rotationally bias the linkages.

In another aspect, the method may include connecting a link to the profiling device or removing a link from the imaging device such that the plurality of links is a number of links determined from an individualized assessment of the configuration of the part of the body that includes the bone fragments.

In another aspect, the at least one biasing element may be at least one spring.

In another aspect, the at least one biasing element may be at least one electromechanical actuator.

In another aspect, the profiling device is one or both of an imaging device and a measuring device.

In accordance with another aspect of the present disclosure, bone fragments of a patient may be tracked. In such aspect, a set of signal transmitters may be placed at least partially around a set of bone fragments. Acoustic signals may be transmitted from the transmitters across the bone fragments to ascertain details of an injury to the bone fragments.

In another aspect, the signal transmitters may be acoustic wave transmitters.

BRIEF DESCRIPTION OF THE DRAWINGS

A more complete appreciation of the subject matter of the present invention and various advantages thereof may be realized by reference to the following detailed description and the accompanying drawings, in which.

DETAILED DESCRIPTION

Figure 1:
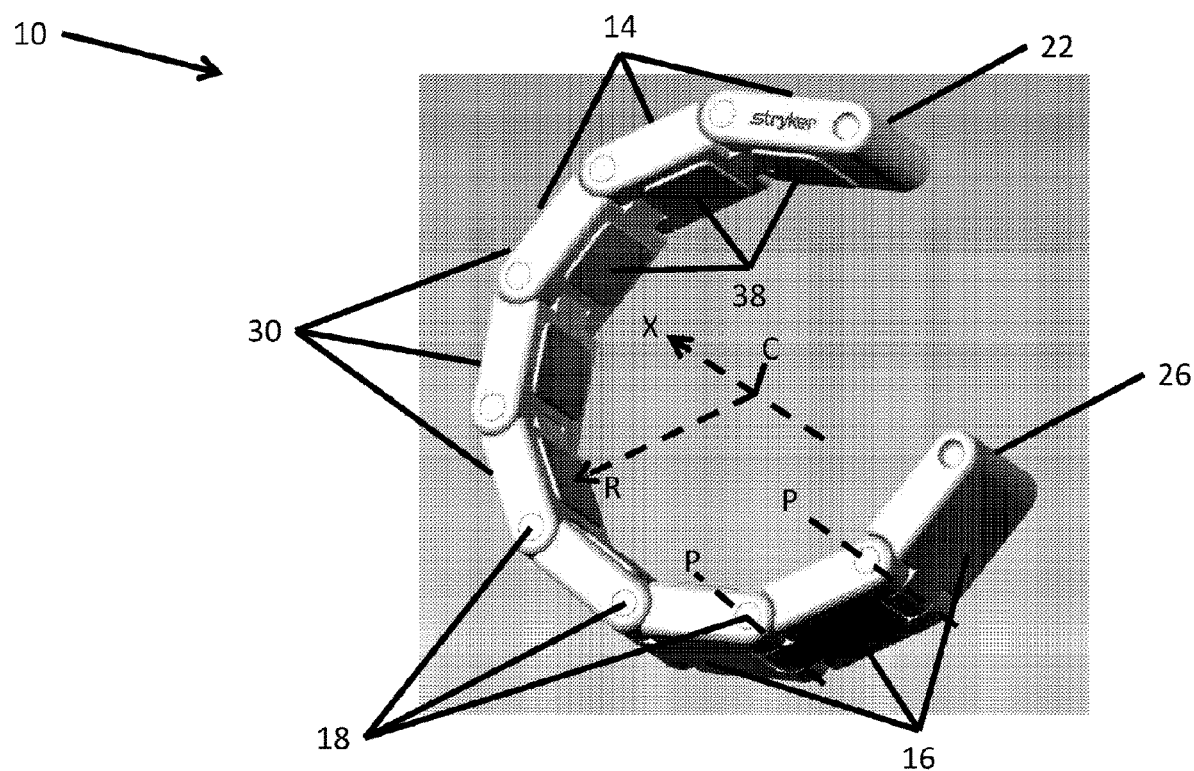
FIG. 1 is a perspective view of a profiling device according to an embodiment.

As shown in FIG. 1, a body profiling device 10 includes a linkage provided by a plurality of pivotally connected links 14. Each adjacent pair of links 14 is joined by a pivotal connection or hinge 18 such that the links may be rotated relative to each other.

The linkage provided by the links 14 includes a first terminal link 22 and a second terminal link 26 on opposite ends of a series of middle links 30. The terminal links 22, 26 are each pivotally connected to only one adjacent link 14. By contrast, each middle link 30 is pivotally connected to two adjacent links 14. In some alternative arrangements, the device may include any one or any combination of more than two terminal links and middle links 30 connected to more than two adjacent links.

As shown, the links 14 each include a tablet shaped housing 16, which as in this example may be rigid. In alternative arrangements, the links may have different shapes and may be more flexible. Each link 14 further includes at least one probe 38. As in the example shown, each probe 38 may include any one or any combination of a transmitter, receiver, transceiver, and other transducer. As in the example shown, the probes 38 may include ultrasound transceivers. A variety of probes 38 are contemplated as suitable for this purpose, e.g., linear, curvilinear, phase array, and mechanical "wobbler" ultrasound probes 38. According to various arrangements, each probe 38 is contained at least partially within a respective housing 16, disposed at least partially outside the respective housing 16, or disposed entirely outside the respective housing 16. In other arrangements, each probe 38 is elastically connected to a respective housing 16 by a linear biasing element such as a spring that biases the probe 38 in a direction perpendicular to a surface of the housing. The position of the linear biasing element may be measured electronically to register contact between the probe 38 or housing 16 and an opposing surface, such as a body being profiled.

Still referring to FIG. 1, each hinge 18 permits and constrains an adjoining pair of links 14 to pivot relative to each other about a pivot axis P defined by the hinge 18. The hinges 18 are respectively arranged such that the pivot axes P are parallel. The device 10 therefore may rest in a generally arcuate or "C" shape centered about a central axis X extending. A radial direction R of the device is defined perpendicularly to the central axis X. In alternative arrangements, the hinges 18 may be pivotal connections that permit adjoining links 14 to pivot about multiple axes while still being attached to each other.

According to certain embodiments, the hinges 18 also include angular biasing elements to bias pivotally connected links 14 relative to one another. The angular biasing elements may each share a common orientation to constrict the device 10 around the central axis X. According to various further embodiments, the angular biasing elements either constrict the links 14 toward each other until rotation of the links are mechanically obstructed, or the angular biasing elements each have a rest point. In this manner, the device 10 may be maintained at rest with a uniform radius along an entire arc defined by the device. In the example shown, the hinges 18 have angular biasing elements with a rest point such that the device 10 is biased toward a rest position in which each link 14 is an equal distance along the radial direction R from the central axis X, as shown in FIG. 1, and thus define a profile in the shape of an open circle. However, devices 10 according to other embodiments have resting positions having a profile in the form of other shapes, which may be regular shapes, e.g., ovals, rectangles, triangles, or which may be irregular shapes and which may be open or closed shapes.

Figure 2:
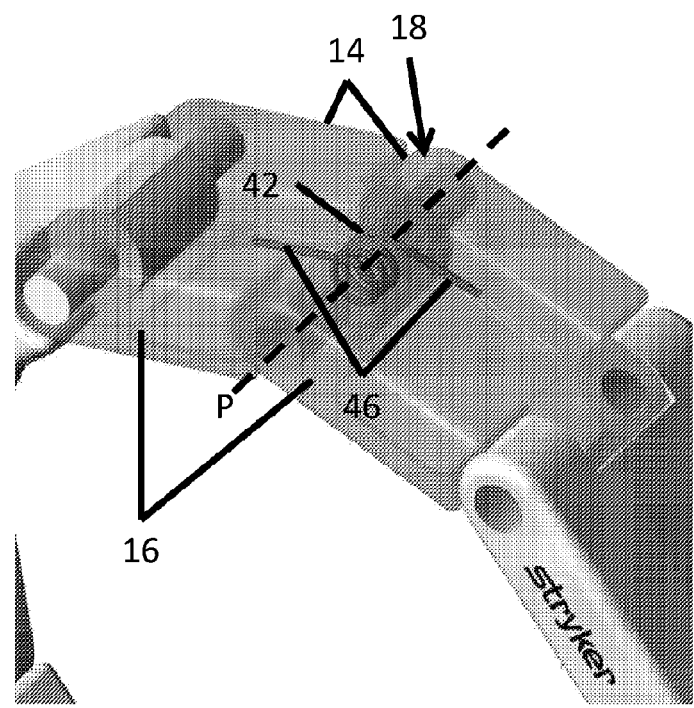
FIG. 2 is a perspective view of a portion of a profiling device according to another embodiment.

Referring now to FIG. 2, in which the adjoining links 14 are shown as transparent for illustration purposes, the hinge 18 includes a spiral spring 42 centered and coiled along the pivot axis P defined by the hinge to act as an angular biasing element. The spring 42 includes two opposite spring ends 46. Each of the spring ends 46 extends into an opposite one of the adjoining links 14. The spring ends 46 are fixed to their respective adjoining link 14 such that the links 14 are pivotally biased with respect to one another about the hinge 18 and the pivot axis P by the spiral spring 42.

Figure 3:
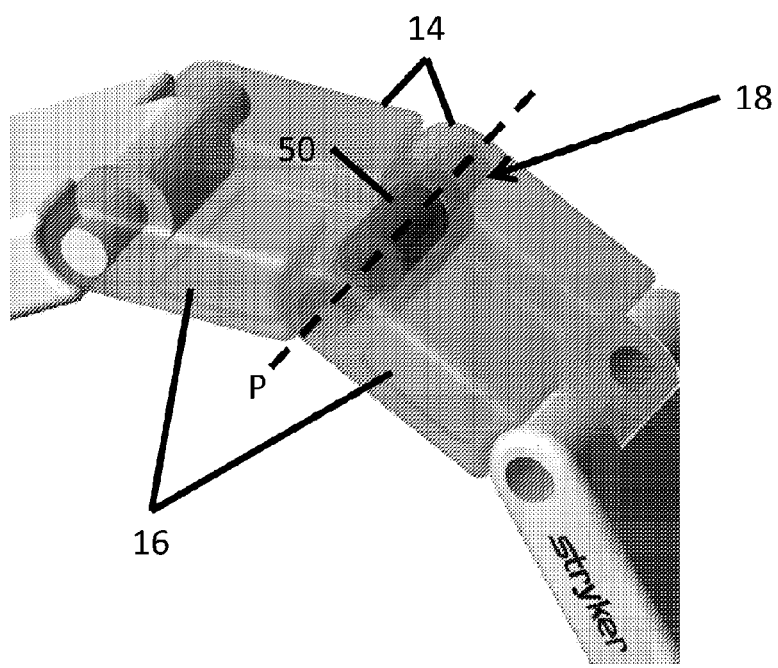
FIG. 3 is a perspective view of a portion of a profiling device according to another embodiment.

As shown in FIG. 3, in another arrangement, hinge 18 includes an electromechanical angular biasing element 50 disposed along the pivot axis P defined by the hinge. The electromechanical angular biasing element 50 preferably may be any suitable electric motor known to those skilled in the art, such as a servo motor, fixedly connected to both adjoining links 14 so as to pivotally bias the adjoining links 14 relative to one another about the hinge 18.

Figure 4A:
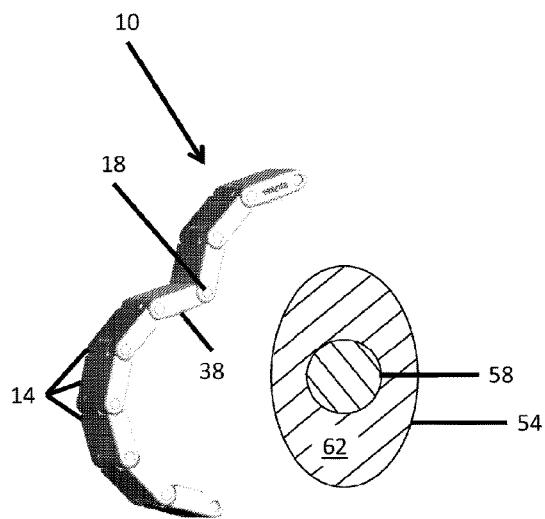
FIG. 4A is a schematic illustration of the profiling device of FIG. 1 shown in an expanded state adjacent to an object to be measured shown in cross-section.
Figure 4B:
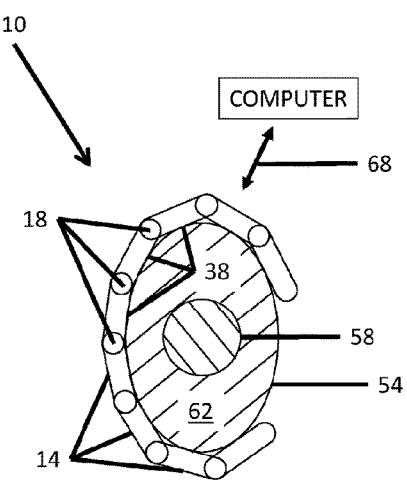
FIG. 4B is a schematic illustration of the profiling device of FIG. 1 wrapped around the object of FIG. 4A shown in cross-section.

FIGS. 4A and 4B illustrate exemplary steps for using the device 10. In the step demonstrated in FIG. 4A, the device 10 is positioned in an expanded state near an object 54. In the example shown, the object 54 is a part of a patient subject, such as an injured limb, that contains a bone 58 disposed within soft tissue 62. Stretching the device 10 to the expanded state may include rotating at least one of the links 14 relative to at least one other link 14 in opposition to any angular biasing elements between the links 14. The device 10, once in the expanded state, is positioned such that the probes 38 are oriented generally toward the subject 54.

In the step shown by FIG. 4B, the device 10 is wrapped around the majority of subject 54. In certain arrangements, the wrapping may occur as a result of the angular biasing elements constricting the device 10 around the subject 54. In this manner, the angular biasing elements act to conform the device 10 to the subject 54. For example, the wrapped device 10 as illustrated in FIG. 4B is generally conformed to an oval shape of the subject 54 such that each of the links 14 contacts the subject 54. The angular biasing elements thereby act to facilitate effective contact between the probes 38 and the subject 54. As described above with respect to the connection of the probes 38 to housings 16, certain embodiments of the device 10 include linear biasing elements between each probe 38 and a respective link 14 which further contribute to effective contact between the probes 38 and the subject 54. As previously noted, the position of the linear biasing elements can be measured electronically or otherwise to register effective contact between the probes 38 and the subject 54.

Figure 5:
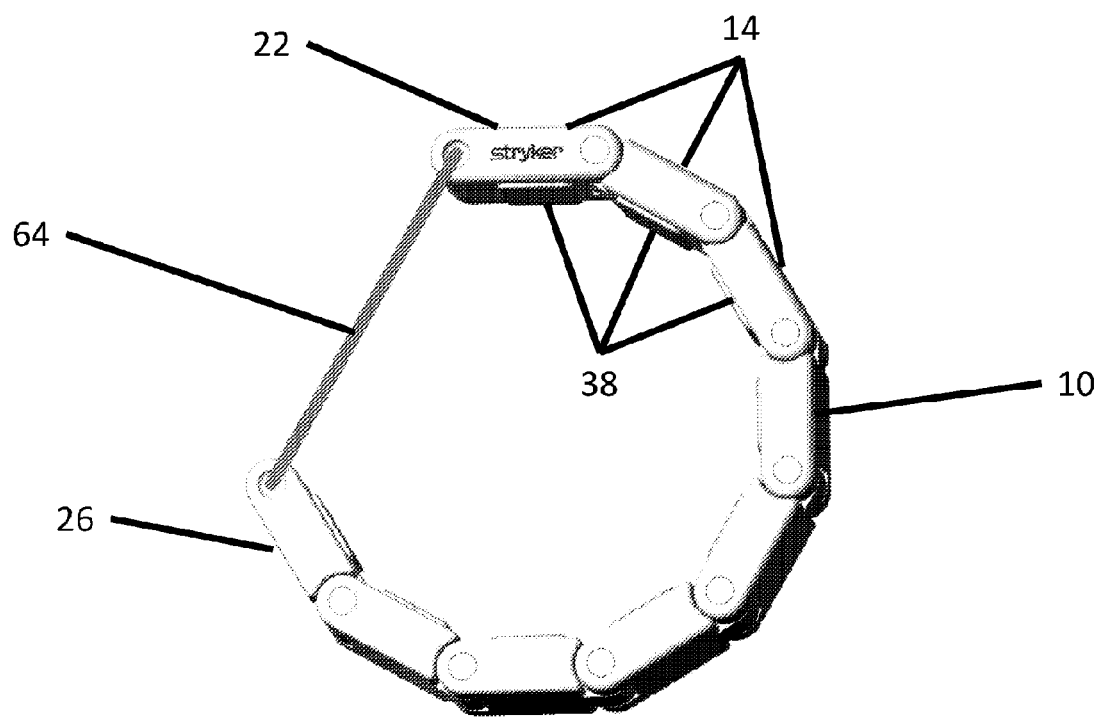
FIG. 5 is a perspective view of a profiling device secured with a strap in accordance with another embodiment.

In other arrangements, the wrapping may be accomplished by manually pressing or pulling the links 14 tight against the subject 54. In such arrangements, the device 10 may be held in place by a tether such as the strap 64 as shown in FIG. 5 and described further herein, an adhesive or other tacky substance applied to the subject 54 or the device 10, or friction in the hinges 18. In still other arrangements, a Bowden cable or other similar cable arrangement runs through the links 14 along an entire length of the device 10 to permit tightening and loosening of the device 10 by manipulation of the cable. The cable itself may also be preloaded with a biasing element, for example, a spring. In yet another arrangement, some or all of the links 14 have docking ports or other coupling features for mechanically coupling to known targeting sleeves to facilitate pin or screw placement such as for use in a biopsy.

The device 10, when wrapped around the subject 54 such that the probes 38 are in effective contact with the subject 54, may be used for measuring or imaging the bone 58 through the soft tissue 62 as shown in FIG. 4B. Measuring and imaging may be accomplished by transmitting a signal, which preferably may be an acoustic signal such as an ultrasonic signal, from one or more of the probes 38 and receiving the signal with one or more of the probes 38, and then processing the received signal. Because ultrasonic signals are generally harmless and may be generated with light and portable equipment, the device 10 according to such exemplary embodiments may be used for live tracking and imaging of the bone 58 over an extended period of time. In certain arrangements, the measuring and imaging can include algorithmic determination of bone density near the measurement site. The determination of bone density can be used to identify suitable screw placement such as for the above described biopsy.

In certain arrangements, the processing of the signal is accomplished with one or more onboard processors housed by the device 10, either in a single link 14 or distributed such that each link 14 houses a processor corresponding to the probe 38 in the same link, or by a computer with which the device 10 is in wired or wireless communication 68 as shown in FIG. 4B. In further embodiments, data from the device 10 is provided to the computer by a known removable storage device, such as a secure digital memory card.

In certain arrangements, the processing is distributed such that one or more onboard processors housed by the device 10 perform certain parts of the image processing, such as imaging, determining a number of actively connected links 14 in the device 10, determining relative positions of the links 14, or aggregating data received from other onboard processors. In an example of such aggregation, the onboard processors may determine an order of priority or work from a predetermined order of priority which may correspond to an order in which the links 14 housing the onboard processors are physically connected or arranged. Data from each onboard processor is communicated to the onboard processor of the next highest priority wirelessly, through one or more cables running between links 14, or through contacts at each hinge 18. The aggregation performed by an aggregating onboard processor may include receiving images generated by one or more onboard processors of higher priority, incorporating signal data from probes 38 corresponding to the one or more onboard processors of higher priority into an image generated or received by the aggregating onboard processor, or discarding or summing duplicative image or signal data received from the onboard processors of higher priority. The data is finally aggregated at an onboard processor of lowest priority, which may be housed in a terminal link 22, 26, that communicates with a computer.

The device 10 may be provided with certain accessories to contribute to secure fastening and ease of use. For example, the first terminal link 22 may be connected to the second terminal link 26 with a strap 64 as shown in FIG. 5. The strap 64, which may be either elastic or of a fixed length depending on a given application, acts to close and maintain the linkage of the device 10 in a loop. The closed loop acts to secure the device 10 around a subject and prevent slipping.

Figure 6:
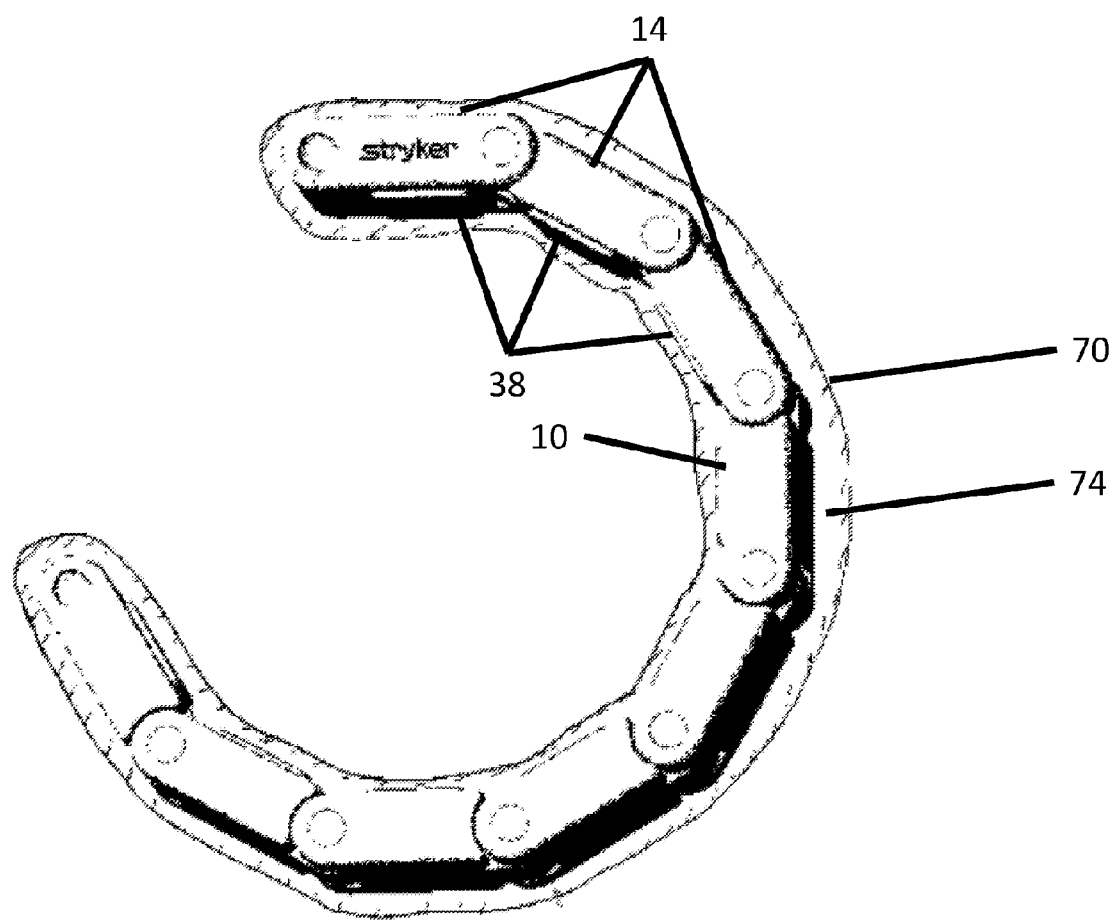
FIG. 6 is a schematic illustration of the profiling device of FIG. 1 shown enclosed in a flexible cover in accordance with another embodiment.

In another example, the linkage device 10 may be enclosed by a flexible cover 70 as illustrated in FIG. 6. The cover 70 aids in sanitation of the device 10 and according to various arrangements is either permanent or disposable. Where disposable covers are employed, a new cover 70 may be applied upon every use of the device 10. When a permanent cover is employed, the cover 70 may be sanitized while protecting the device 10 from intrusion by sanitizing agents. The cover 70 can also contribute to effective contact between the device 10 and a subject. As illustrated, the cover 70 may be filled with a coupling medium 74 such that the cover 70 will conform to a subject when the device 10 is applied to provide continuous effective contact along an entire length of the device 10. Additional medium 74 may be applied outside of the cover 70 as well to further improve effective contact. In arrangements in which the probes 38 are ultrasound probes, the medium 74 may be a known acoustic coupling gel. In other arrangements, cover 70 may be constructed from a flexible material with embedded ultrasound transducers such that coupling gel is unnecessary.

Figure 7:
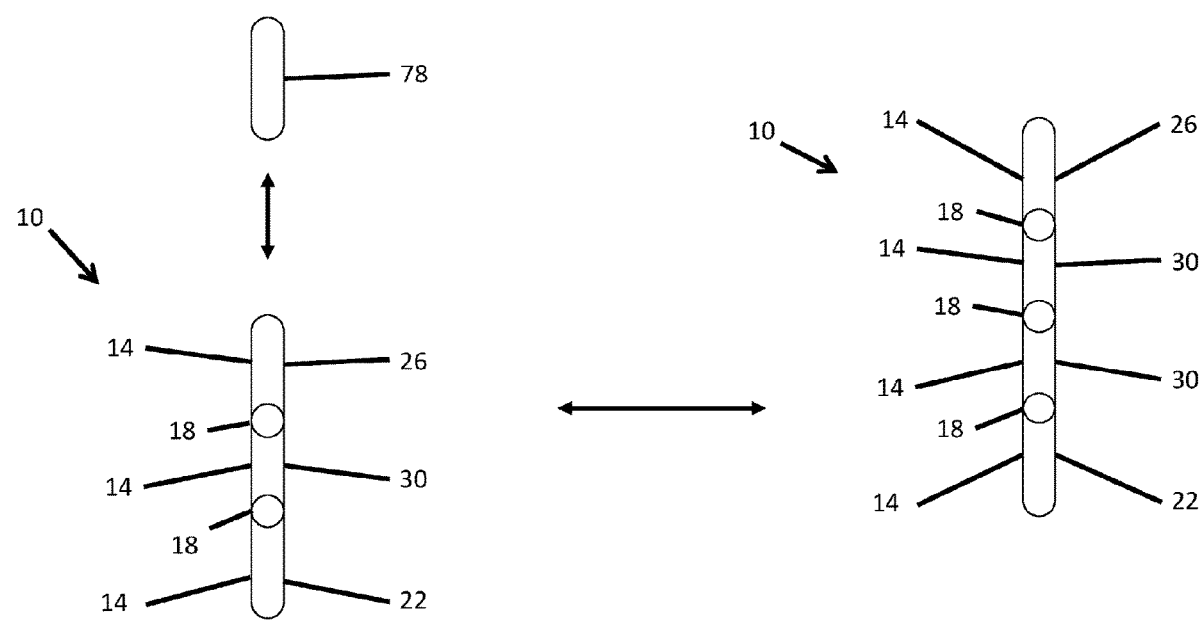
FIG. 7 is a schematic illustration of modular connections and disconnections of a link of a profiling device in accordance with an embodiment.

As shown in FIG. 7, according to certain embodiments, the device 10 is of a modular construction such that links 14 may be added or removed from the device 10 as appropriate for a given object, such as object 54 shown in FIGS. 4A and 4B. For example, an appropriate number of links 14 for a given application may be determined in an individualized assessment of the subject 54, such as by calculating an appropriate number of links for optimal data acquisition based on a circumference or other perimeter, thickness, and shape, of a part of the subject 54 to be either one or both of measured or imaged, which may be determined prior to applying the device 10 to the subject 54. In various modular arrangements, the links 14 are operatively connectable and disconnectable from each other such that the device 10 operates generally similarly regardless of a number of active links 14, but power, data, or both are communicated between operatively connected links 14. As illustrated in FIG. 7, a free link 78 may be connected to or disconnected from the second terminal link 26. The second terminal link 26 may be reversibly converted to a new middle link 30 while the free link 78 is reversibly converted to a new second terminal link 26. Alternatively, the second terminal link 26 is converted to a new free link 78 while a middle link 30 adjacent to the second terminal link 26 is converted to a new second terminal link 26. The operable connection between the links 14 may include one or more cables running along the device 10 or contacts at each hinge 18 that facilitate communication between probes 38 or onboard processors housed by the links 14. According to certain further arrangements, the processor, processors, or computer responsible for processing the signals from the probes 38 is able to detect a number of active or operatively connected probes 38 and adjust the image processing accordingly.

In certain of the modular arrangements with at least one onboard processor, the first terminal link 22 functions as a base link in that the link includes a first primary processor, whereas the middle links 30 each contain either no onboard processor or an auxiliary processor. In some arrangements, the second terminal link 26 includes either no onboard processor or an auxiliary processor, consistent with the presence or absence of auxiliary processors within the middle links 30, or the second terminal link 26 includes a second primary processor which may or may not differ from the first primary processor. The one or more primary processors differ from any auxiliary processors. For example, the one or more primary processors may perform an aggregation process not performed by any auxiliary processors, or may include features, such as a transmitter and a receiver or a transceiver for wirelessly communicating with a central processor of the computer or a port for a wired connection with the computer. The central processor may be part of the ADAPT® Platform for surgical navigation by Stryker Corporation or other central assistance system which may communicate with other devices, a hospital network, or other networks through cloud-based servers.

According to certain arrangements, the device 10 is capable of tracking or measuring relative angular or absolute positions of the links 14 joined by each hinge 18. Angular measuring features at the hinges 18 may include transducers, piezoelectric elements in or connected to springs 42, servo motors as electromechanical angular biasing elements 50, or other known features for measuring angles. According to other embodiments, one or more onboard processors within the device 10 or an associated computer compute the relative positions of the links 14 or probes 38 using signal data from the probes 38. For example, any of the housings 16, hinges 18, probes 38, and springs 42 or motors 50 are opaque to a variety of signal sent and received by the probes 38, with other parts of the device 10 being translucent or transparent to the variety of signal sent and received by the probes 38. According to further embodiments of the above, any of the above mentioned parts of the device 10 could be generally translucent or transparent but provided with distinctive opaque marking patterns shaped to facilitate detection during image processing. In such arrangements, the contrast between opaque and transparent or translucent parts enables the image processing software to identify and locate the opaque parts within the signal data to determine the relative positions and orientations of the links 14 or probes 38. In yet further embodiments, any of the above mentioned parts of the device 10 could be radiopaque or include radiopaque marking patterns for co-registration of the device 10 in fluoroscopy. In still further embodiments, relative positions of the links 14 are determined through beamforming techniques such as determining a location of a transmitter by a strength or phase of the transmitter's signal at a corresponding receiver or computed from a delay between a time that a signal is transmitted by one probe 38 and a time that the signal is received by one or more other probes 38.

It is to be understood that the disclosure set forth herein includes any possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments in accordance with the invention.

Furthermore, although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended numbered paragraphs below.

The invention claimed is:

1. A body profiling device, comprising:
a plurality of pivotally connectable links;
a plurality of rigid enclosures, wherein each of the plurality of pivotally connectable links includes a rigid enclosure of the plurality of rigid enclosures; and
a plurality of probes, each of the plurality of probes being disposed on a link of the plurality of pivotally connectable links entirely outside of a corresponding rigid enclosure of the plurality of rigid enclosures and including any one or any combination of a transmitter configured to send a signal, a receiver configured to receive the signal, and a transceiver configured to send and receive the signal.

2. The body profiling device of claim 1, further comprising:
a plurality of hinges, each of the plurality of hinges being attachable to adjoining links of the plurality of pivotally connectable links to define pivot axes such that the adjoining links pivot about a respective one of the pivot axes defined by a hinge of the plurality of hinges to which the adjoining links are attached.

3. The body profiling device of claim 2, wherein at least one of the plurality of hinges includes a spiral spring configured to be coiled around a corresponding pivot axis of the pivot axes.

4. The body profiling device of claim 2, wherein at least one of the plurality of hinges includes an electromechanical actuator configured to pivotally bias the adjoining links.

5. The body profiling device of claim 2, wherein the plurality of hinges are configured to measure an angular position between adjacent links.

6. The body profiling device of claim 1, wherein the signals are acoustic.

7. The body profiling device of claim 1, wherein the body profiling device is either one of or both an imaging device and a measuring device.

8. The body profiling device of claim 1, wherein the plurality of links are connected to form a linkage, further comprising:
a flexible cover that completely covers the linkage.

9. The body profiling device of claim 8, further comprising an acoustical coupling fluid applied to the flexible cover.

10. The body profiling device of claim 8, wherein the flexible cover is filled with an acoustical coupling medium.

11. The body profiling device of claim 1, wherein:
some of the plurality of pivotally connectable links are middle links pivotally connected to two adjacent links; and
two of the plurality of pivotally connectable links are terminal links pivotally connected to only one adjacent link.

12. A body profiling system, comprising:
the body profiling device of claim 1; and
a computer processor, wherein:
the plurality of pivotally connectable links are connected to form a linkage and include a first link, a second link, a third link, and a fourth link, wherein:
the first link includes a first transmitter and the second link includes a first receiver, the first receiver opposing the first transmitter such that the first receiver receives a first ultrasonic signal from the first transmitter,
the third link includes a second transmitter and the fourth link includes a second receiver, the second receiver opposing the second transmitter such that the second receiver receives a second ultrasonic signal from the second transmitter, and
the computer processor is configured for electronically communicating with the first and the second transmitters and the first and the second receivers to determine a position of an object at least partially surrounded by the body profiling device.

13. A method of tracking bone fragments of a patient comprising:
positioning the body profiling device of claim 1 near a part of a body of the patient that includes the bone fragments;
allowing at least one angular biasing element of the profiling device to conform the profiling device to the part of the body of the patient; and
interpreting acoustic signals transmitted across the bone fragments to ascertain either one of or both a relative location and a relative orientation of the bone fragments.

14. A body profiling system, comprising:
a plurality of pivotally connectable links;
a plurality of probes, each of the plurality of probes disposed on a link of the plurality of pivotally connectable links and including any one or any combination of a transmitter configured to send a signal, a receiver configured to receive the signal, and a transceiver configured to send and receive the signal; and
a computer processor, wherein:
(i) the plurality of pivotally connectable links are modularly and operatively interconnectable with each other:
to reversibly and operatively connect a new link to a terminal link, thereby converting the terminal link to a middle link and the new link to a new terminal link; or
to reversibly and operatively disconnect the terminal link, thereby converting an adjacent link to the terminal link to a new terminal link; and
(ii) the computer processor is configured for determining an order of priority in which to aggregate signal data from the links and electronically communicating with the plurality of probes.

15. The body profiling system of claim 14, wherein the terminal link houses the computer processor.

16. The body profiling system of claim 14, further comprising a computer system that includes the computer processor, the computer processor being located remotely from the plurality of pivotally connectable links.

17. The body profiling system of claim 16, wherein at least some of the plurality of probes are configured to communicate wirelessly with the computer system.

18. The body profiling device of claim 14, wherein the computer processor is configured to determine either one of or both relative positions of the links and a number of operatively connected links.

19. A body profiling device, comprising:
- a plurality of pivotally connectable links;
- a plurality of enclosures, wherein each of the plurality of pivotally connectable links includes an enclosure of the plurality of enclosures; and
- a plurality of probes, each of the plurality of probes being disposed on a link of the plurality of pivotally connectable links entirely outside of a corresponding enclosure of the plurality of enclosures and including any one or any combination of a transmitter configured to send a signal, a receiver configured to receive the signal, and a transceiver configured to send and receive the signal, wherein at least one probe is elastically connected to a corresponding link of the plurality of pivotally connectable links by a linear biasing element configured for biasing the probe into contact with a body being profiled.

20. The body profiling device of claim 19, wherein the linear biasing element is a spring.

* * * * *